United States Patent [19]

Yatvin et al.

[11] Patent Number: 5,256,641
[45] Date of Patent: Oct. 26, 1993

[54] COVALENT POLAR LIPID-PEPTIDE CONJUGATES FOR IMMUNOLOGICAL TARGETING

[75] Inventors: Milton B. Yatvin, Portland, Oreg.; Michael H. B. Stowell, Pasadena, Calif.; Miroslav Malkovsky, Madison, Wis.

[73] Assignee: State of Oregon, Portland, Oreg.

[21] Appl. No.: 911,209

[22] Filed: Jul. 9, 1992

Related U.S. Application Data

[63] Continuation-in-part of Ser. No. 607,982, Nov. 1, 1990, Pat. No. 5,149,794.

[51] Int. Cl.$^5$ .................. A61K 31/00; A61K 31/685; A61K 31/19; A61K 37/02
[52] U.S. Cl. .......................................... 514/2; 514/78; 514/557; 514/885; 530/300; 530/329; 530/331
[58] Field of Search .................. 514/2, 78, 557, 885; 530/300, 329, 331

[56] References Cited

PUBLICATIONS

Wiesmüller et al., 1991, Immunology 72:109-113.
Frisch et al., 1991, Eur. J. Immunol. 21:185-193.
Falk et al., 1991, Nature 351:290-296.
Germain & Hendrix, 1991, Nature 353:134-139.
Sadegh-Nasseri and Germain, 1991, Nature 353:167-170.
Jardetzky et al., 1991, Nature 353:326-329.
Lanzavecchia et al., 1992, Nature 357:249-252.
Guéry et al., 1992, J. Exp. Med. 175:1345-1352.
DeMagriatis et al., 1992, Cell 68:625-634.
Lamont et al., 1990, J. Immunol. 144:2493-2498.
Elliott et al., 1990, Nature 348:195-197.
Falk et al., 1990, Nature 348:248-251.
Parham, 1990, 1990, Nature 348:674-675.
Abbas, Lichtman and Pober, 1991, Cellular and Molecular Immunology (W. B. Saunders Co.: Philadelphia), pp. 116-136.
Faustman et al., 1991, Science 254:1756-1771.
Hopp, 1984, Mol. Immunol. 21:13-16.
Neurath et al., 1984, J. Gen. Virol. 65:1009-1014.
Deres et al., 1989, nature 342:561-564.
Vandenbark et al., 1989, Nature 341:841-844.
Seifert et al., 1990, Biochem. J. 267:795-802.
Brynestad et al., 1990, J. Virol. 64:680-685.

*Primary Examiner*—John W. Rollins
*Attorney, Agent, or Firm*—Allegretti & Witcoff, Ltd.

[57] ABSTRACT

This invention relates to methods of facilitating the entry of peptides into cells and targeting such peptides to specific organelles within the cell. The invention provides methods for delivering and specific targeting of antigenically-active peptides to cells for the specific production of immunological reactivity against such peptides, as well as compositions and pharmaceutical compositions of matter comprising such peptides. This invention thereby provides improved methods for vaccine production and in vivo vaccination against pathogenic microorganisms. Methods for alleviating autoimmune disease and ameliorating tissue and organ transplant rejection using such conjugates are also provided.

23 Claims, 8 Drawing Sheets

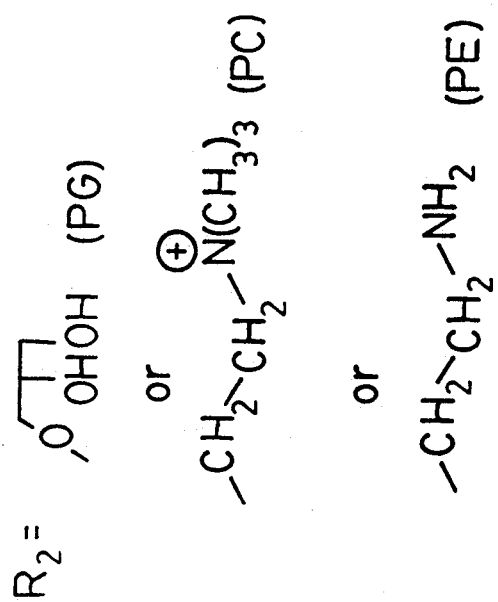
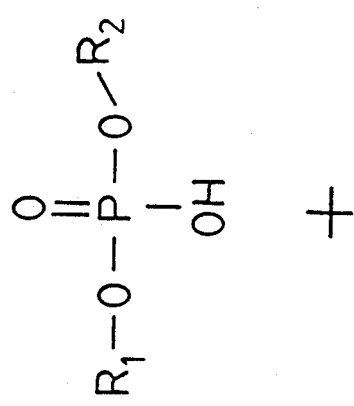
FIG. 4
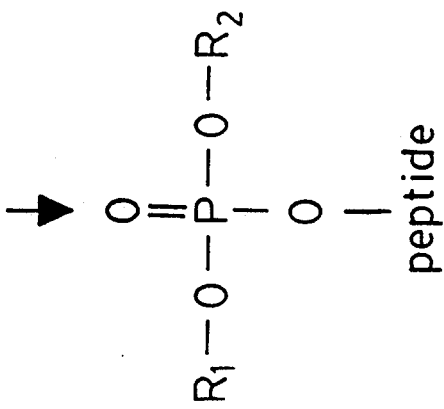
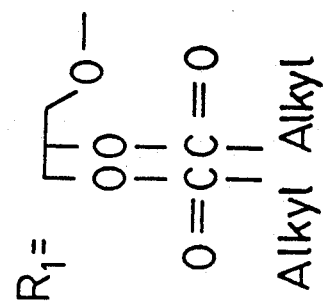

FIG. 6 cont'd
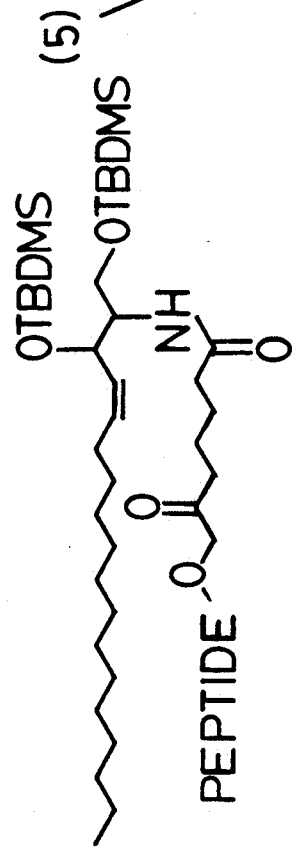
(5)
→ ROOM TEMP TETRABUTYLAMMONIUM FLUORIDE
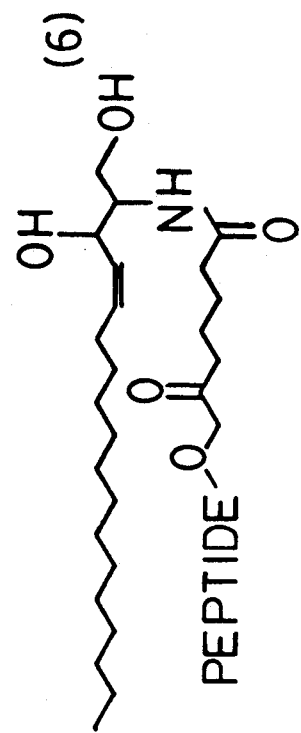
(6)

FIG. 7
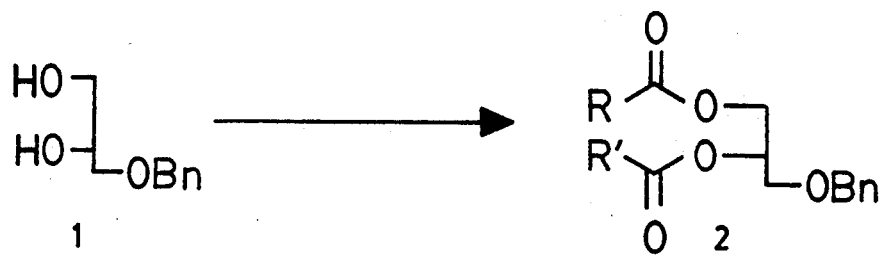
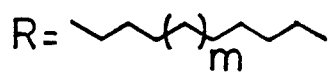
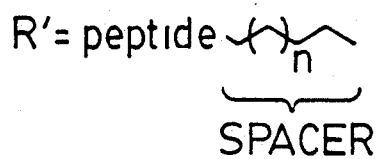
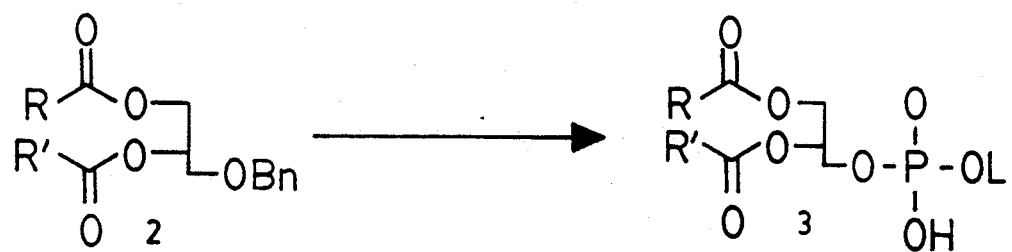
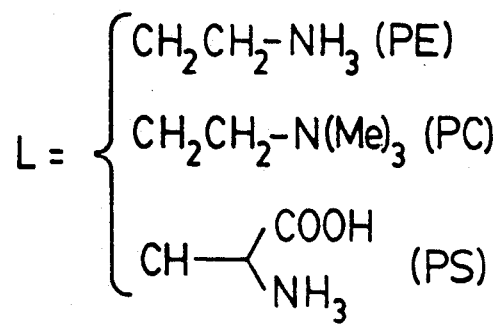

COVALENT POLAR LIPID-PEPTIDE CONJUGATES FOR IMMUNOLOGICAL TARGETING

BACKGROUND OF THE INVENTION

This invention was made with government support under grants 1-R01-CA49416 and RR-00167 by the National Institutes of Health. The government has certain rights in the invention.

This application is a continuation-in-part of U.S. patent application Ser. No. 07/607,982, filed Nov. 1, 1990, now U.S. Pat. No. 5,149,794, which is herein incorporated by reference.

1. Field of the Invention

This invention relates to a method of facilitating the entry of peptides into cells and also a method of targeting such peptides to specific organelles within the cell. More specifically, this invention provides methods related to delivering antigenically-active peptides for the specific production of immunological response against such peptides. As such, this invention provides improved methods for vaccine production and in vivo vaccination against pathogenic microorganisms. In particular, the invention provides polar lipid/peptide conjugates that mediate specific targeting of peptides to subcellular organelles in appropriate cells of the immune system of vertebrates, including man. The invention also provides pharmaceutical compositions of such polar lipid/peptide conjugates. Methods for alleviating autoimmune disease and ameliorating tissue and organ transplant rejection using such conjugates are also provided.

2. Information Disclosure Statement

Vertebrate immunological response to antigenic stimuli depend on a phenomenon called presentation of antigens. Presentation embodies the appearance of antigenic epitopes on the cell surface of antigen-presenting cells of the immune system in association with major histocompatibility complex (MHC) proteins. The MHC proteins are divided into 2 classes (I and II) whereby each class presents antigens derived from different sources. The two types of immune response corresponding to presentation via the two types of MHC molecules are immunity requires presentation of peptide antigens in association with MHC molecules (see, Abbas, Lichtman and Pober, 1991, *Cellular and Molecular Immunology* (W. B. Saunders Co.: Philadelphia), pp. 116-136 for review).

In the class I restricted immune response, MHC class I molecules are associated with peptide antigens derived from proteins made intracellularly. Such proteins include proteins encoded by viruses and other intracellular pathogens. These proteins are degraded in the cytoplasm of infected cells, and the peptide products of this degradation transferred into the endoplasmic reticulum (ER) via the action of peptide-specific transporter molecules located in the ER membrane (see, Elliott et al., 1990, Nature 348: 195-197; Parham, 1990, Nature 348: 674-675). Nascent MHC class I molecules synthesized in the ER are assembled into functional presenting proteins only in the presence of the appropriate peptide antigen. Fully assembled MHC class I complexes are then transported through the Golgi apparatus to the cell surface, where the antigen presenting complex can activate a cellular (T-cell mediated) immune response by interacting with CD8+ cytotoxic T-cells (see, Falk et al., 1990, Nature 348: 248-251; Falk et al., 1991, Nature 351: 290-296).

Alternatively, in the MHC class II restricted immune response, extracellular antigens (including free-living pathogens or protein components thereof) are engulfed by cells of the immune system (such as macrophages) by endocytosis, and transferred to the endosomal (lysosomal) compartment for degradation. Peptide products of such degradation may then associate with MHC class II molecules (which molecules lack the requirement of peptide association for cell-surface expression; see, Germain and Hendrix, 1991, Nature 353: 134-139) and appear on the cell surface (see, Sadegh-Nasseri and Germain, 1991, Nature 353: 167-170; Lanzavecchia et al., 1992, Nature 357: 249-252). The MHC class II antigen-presenting pathway leads to the induction of a humoral (antibody-dependent) immune response and the activation of CD4+T-helper cells.

In the preparation and use of vaccines to provoke immunity to pathogenic organisms, the appropriate MHC restriction is achieved using alternative strategies (see, Abbas, Lichtman and Pober, 1991, *Cellular and Molecular Immunology* (W. B. Saunders Co.: Philadelphia), pp. 315 for review). MHC class I restricted immunity requires the use of attenuated pathogenic organisms (usually viruses) which non-productively infect host cells. The protein antigens of the pathogenic organism is degraded intracellularly, and the peptide antigens produced transduced to the ER and assembled into functional MHC class I presentation complexes. Presentation of antigen to cytotoxic T-cells results in cellular immunity against the pathogenic microorganism.

Vaccination using the MHC class II restricted route involves inoculation with inactivated (e.g., chemically inactivated) pathogen, which is then engulfed by macrophages and lysosomally degraded intracellularly. Peptide antigens associated with the appropriate MHC class II complex are then presented to T-helper cells, which cells release cytokines and other immune system stimulating factors, which activate antibody-producing B cells specific for the peptide antigen presented.

Both routes to producing immunity to pathogenic organisms require degradation and selection of the appropriate peptide antigen by the cells of an animals immune system in vivo. This allows for variability in the efficacy of production of the immune response, and in the case of the use of attenuated viruses, the possibility for reversion to pathogenicity (with the result that the vaccine causes the disease it was meant to forestall). There is a need, therefore, for developing methods to efficiently deliver peptide antigens directly to cells of the immune system for presentation to T-cells in association with the appropriately restricted MHC complex.

Similarly, autoimmune disease is related to the presentation and immunological recognition of peptide antigens derived from endogenous cellular proteins (called self-antigens; see, Jardetzky et al., 1991, Nature 353: 326-329; Faustman et al., 1991, Science 254: 1756-1771). Self-antigens may be presented by either the MHC class I or class II restricted pathway, resulting in either cellular or humoral autoimmunity, or both. There is a need to develop methods and reagents to block presentation of self-antigens, thereby ameliorating or preventing the onset of progression of autoimmune disease.

In addition, tissue or organ transplant rejection is mediated by both MHC class I and class II restricted immune response. Non-self antigens are processed and recognized by the immune system of the transplant recipient, causing an immunological attack on the transplant resulting in its rejection by the host. Current methodologies of inhibiting transplant rejection involve suppressing the immune system indiscriminately with drugs such as cyclosporin A. These methods leave the host immune-compromised and at risk for adventitious infection by pathogens. There is a need for methods of selectively blocking host MHC restricted immune response against tissue and organ transplants which do not result in general immune suppression.

The use of peptide antigens as immunogens has been attempted in the prior art, with limited success in vivo.

Hopp, 1984, Mol. Immunol. 21: 13-16 disclosed the use of a synthetic hepatitis viral antigen acylated with a fatty acid moiety as an in vivo immunogen.

Neurath et al., 1984, J. Gen. Virol. 65: 1009-1014 utilize hepatitis surface antigen-derived peptide immunogens that are chemically fixed to liposomes in vitro.

Deres et al., 1989, Nature 342: 561-564 disclose the use of influenza peptide epitopes chemically linked to lipoprotein adjuvants as immunogens in vivo.

Seifert et al., 1990, J. Biochem. 267: 795-802 teach the use of lipoprotein-derived synthetic antigens for activating human neutrophils in vitro.

Brynestad et al., 1990, J. Virol. 64: 680-685 use palmitoylated peptide antigens derived from herpes simplex virus glycoprotein D as immunogens in vivo.

Wiesmüller et al., 1991, Immunology 72: 109-113 demonstrate that synthetic lipoprotein analogues stimulate cytokine release and activate B cells and macrophages in vitro.

Frisch et al., 1991, Eur. J. Immunol. 21: 185-193 describe the use of a histone H3 derived, hexapeptide antigen covalently attached to phosphatidylethanolamine and encapsulated into liposomes for immunizing mice in vivo.

Peptides have also been used for blocking an immune response.

Vandenbark et al., 1989, Nature 341: 841-844 demonstrate that a peptide derived from the T-cell receptor V$\beta$8 chain can be used to block experimentally-induced autoimmune encephalitis (EAE) in vivo.

Lamont et al., 1990, J. Immunol. 144: 2493-2498 disclose peptide MHC class II inhibitors of antigen presentation.

Guéry et al., 1992, J. Exp. Med. 175: 1345-1352 demonstrate inhibition of antigen presentation in vivo using a blocking peptide antigen.

DeMagriatis et al., 1992, Cell 68: 625-634 show the use of an influenza peptide to block T-cell mediated immunity in vitro.

SUMMARY OF THE INVENTION

The present invention is directed to methods for eliciting or inhibiting an immune response in an animal, preferably a human. The invention provides reagents comprising antigenically-active peptides covalently linked to polar lipid carrier molecules. Conjugation of the antigenically-active peptides to the polar lipid can be mediated by a spacer moiety. The choice of polar lipid conjugated to the antigenically-active peptides of the invention will influence the intracellular site to which such peptide/lipid conjugates are targeted. Methods for using the reagents of the invention are also provided.

This invention has the specific advantage of facilitating the entry of antigenically-active peptides into cells of the immune system via a polar lipid carrier, allowing introduction of such peptides into cells in the absence of intracellular production of the peptides and without requiring endocytosis of such peptides into the degradative compartment of such cells. As disclosed herein, the invention comprehends a polar lipid/peptide conjugate wherein the polar lipid will selectively associate with certain biological membranes, and facilitate intracellular localization of the peptides therein.

The polar lipid may be conjugated to the antigenically-active peptide through use of a spacer, which may act to release the peptide from the lipid, target the conjugate to the proper intracellular compartment, or perform other functions to maximize the effectiveness of immunological processing by the cell.

This type of conjugate has numerous advantages. First, this invention will allow the entry of antigenically-active peptides into cells at a pharmokinetic rate. This feature of the invention eliminates the requirement using traditional vaccination methods for intracellular synthesis of viral peptide antigens destined for presentation via the major histocompatibility complex class I antigen presentation pathway. Second, for antigens presented via the major histocompatability complex class II antigen presentation pathway, the specific antigenic epitope can be delivered to the lysosomal compartment of the cell for association with nascent MHC class II molecules without the need for intracellular proteolysis of the cognate protein of the peptide antigen. Third, the reagents of the invention may incorporate a spacer region that can be varied and thereby allow an immunologically-relevant rate of antigen release in antigen-presenting cells.

In a first aspect, this invention provides a composition of matter comprising a peptide, a polar lipid carrier, two linker functional groups and a spacer, wherein the spacer has a first end and a second end and wherein the polar lipid is attached to the first end of the spacer through a first linker functional group and the peptide is attached to the second end of the spacer through a second linker functional group. In a preferred embodiment, the peptide is an antigenically active peptide. In another preferred embodiment, the spacer allows the peptide to act without being released at an intracellular site. In this embodiment of the invention, the covalent attachment of the first linker functional group to the first end of the spacer is weak and the covalent attachment of the second linker functional group to the second end of the spacer is strong; alternatively, both covalent attachments are strong. In other embodiments, the spacer facilitates hydrolytic or enzymatic release of the peptide at an intracellular site. In this embodiment, the covalent attachment of the first linker functional group to the first end of the spacer is strong and the second linker functional group attached to the second end of the spacer is weak. Preferred polar lipids include sphingosine, ceramide, phosphatidyl choline, phosphatidyl glycerol, phosphatidyl ethanolamine, phosphatidyl inositol, phosphatidyl serine, cardiolipin and phosphatidic acid.

A second aspect of the invention provides a composition of matter comprising a peptide having a first functional linker group, and a polar lipid carrier having a second functional linker group, wherein the peptide is covalently linked to the polar lipid carrier by a chemical bond between the first and second functional linker groups. In a preferred embodiment, the peptide is an antigenically active peptide. Preferred first functional linker groups include a hydroxyl group, a primary or secondary amino group, a phosphate group or substituted derivatives thereof and a carboxylic acid group. Preferred second functional linker groups include a hydroxyl group, a primary or secondary amino group, a phosphate group or substituted derivatives thereof and a carboxylic acid group. Preferred polar lipids include sphingosine, ceramide, phosphatidyl choline, phosphatidyl glycerol, phosphatidyl ethanolamine, phosphatidyl inositol, phosphatidyl serine, cardiolipin and phosphatidic acid.

The invention provides a method of immunizing an animal against a pathogenic microorganism, comprising the step of inoculating the animal with a reagent that is a composition of matter of the invention in a pharmaceutically acceptable carrier in an amount sufficient to elicit an immunological response in the animal. The preferred animal is a human being.

The invention also provides a method of alleviating autoimmune disease in an animal, comprising the step of inoculating the animal with a reagent that is a composition of matter of the invention in a pharmaceutically acceptable carrier in an amount sufficient to inhibit the autoimmune response in the animal. The preferred animal is a human being.

The invention further provides a method for preventing tissue or organ transplant rejection in an animal, comprising the step of inoculating the animal with a reagent that is a composition of matter of the invention in a pharmaceutically acceptable carrier in an amount sufficient to inhibit transplant rejection in the animal. The preferred animal is a human being.

Specific preferred embodiments of the present invention will become evident from the following more detailed description of certain preferred embodiments and the claims.

BRIEF DESCRIPTION OF THE DRAWINGS

FIG. 4 depicts the synthetic scheme put forth in Example 4.

FIG. 7 depicts the synthetic scheme put forth in Example 7.

DETAILED DESCRIPTION OF THE PREFERRED EMBODIMENTS

Figure 1:
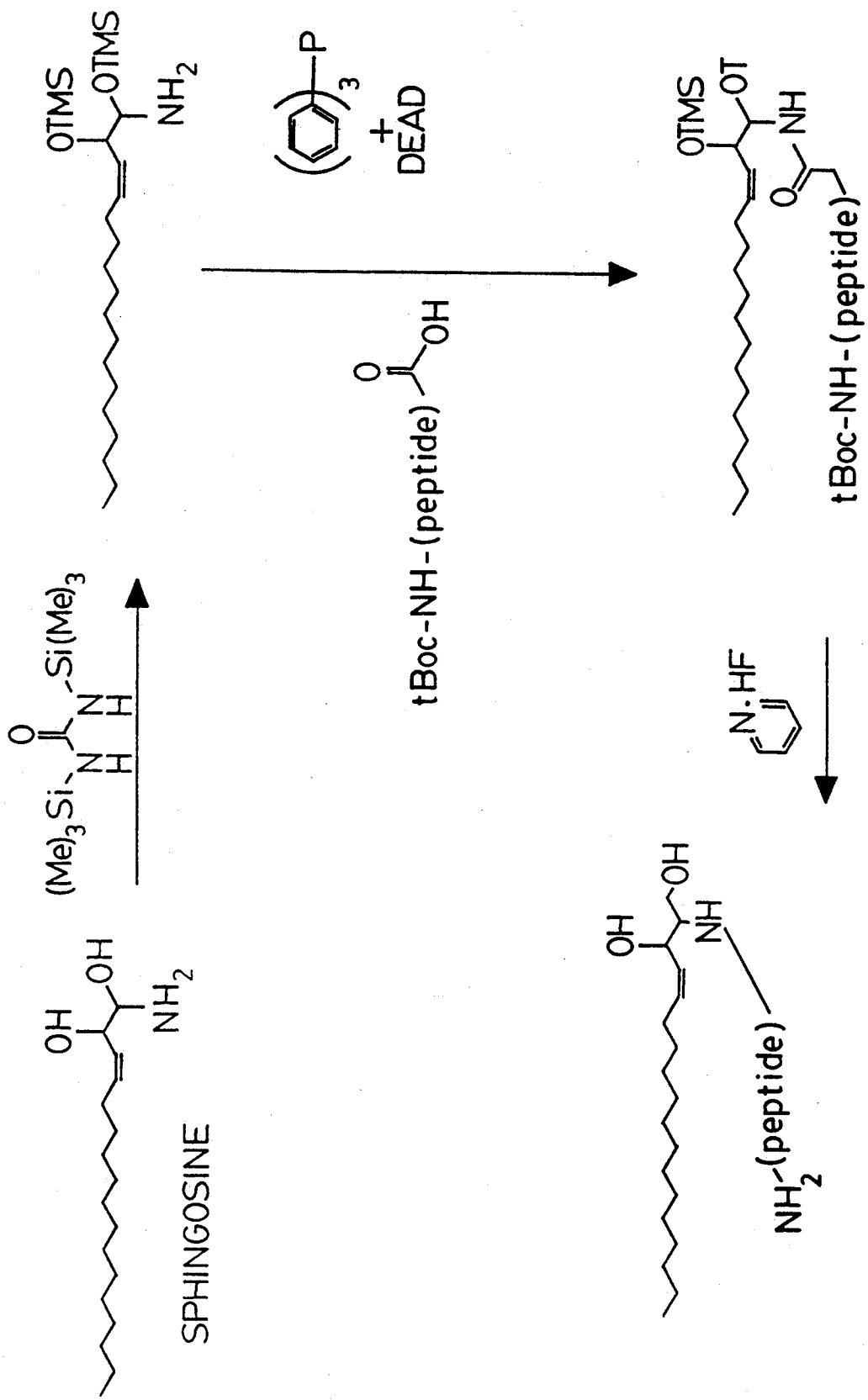
FIG. 1 depicts the synthetic scheme put forth in Example 1.
Figure 2:
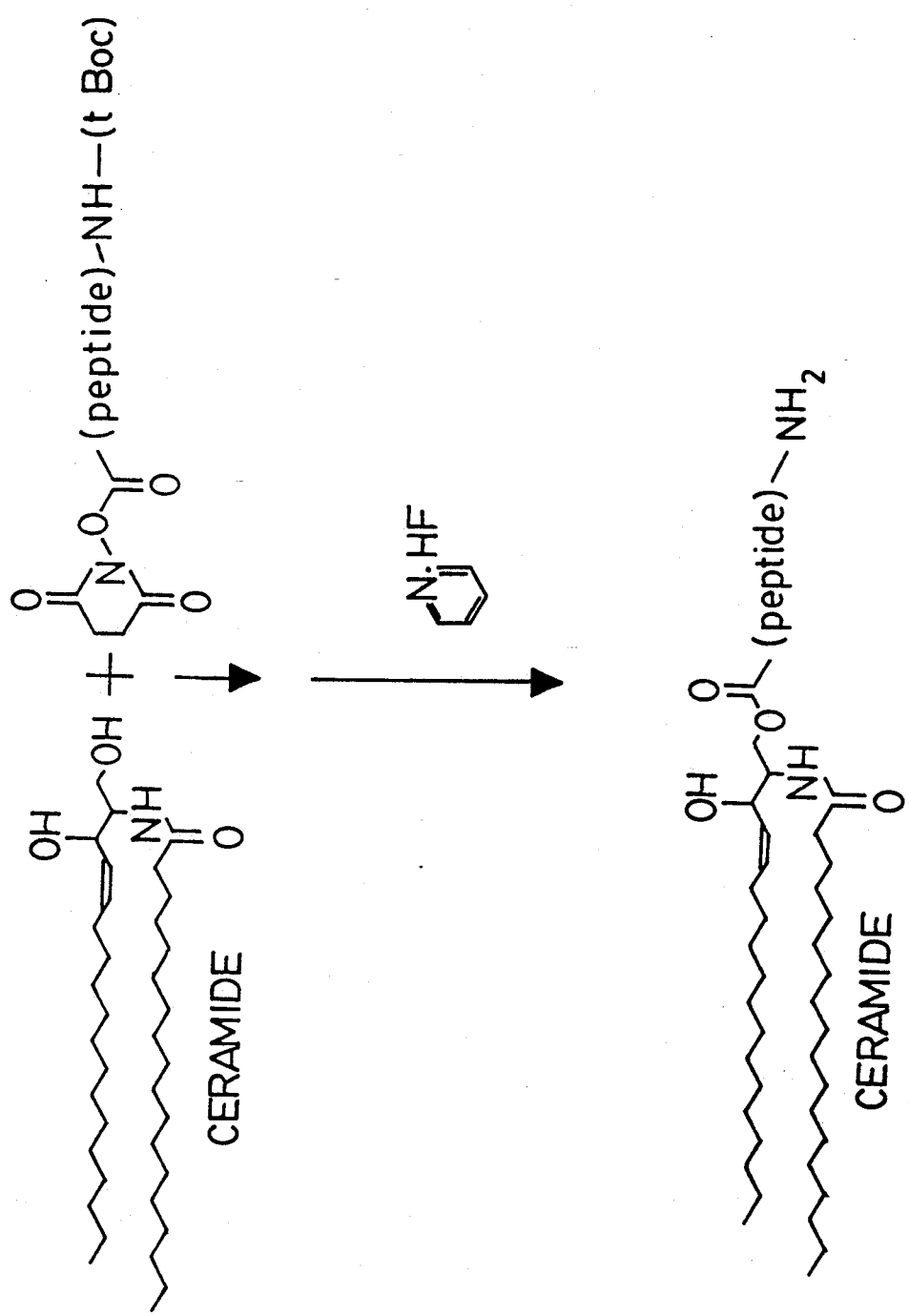
FIG. 2 depicts the synthetic scheme put forth in Example 2.
Figure 3:
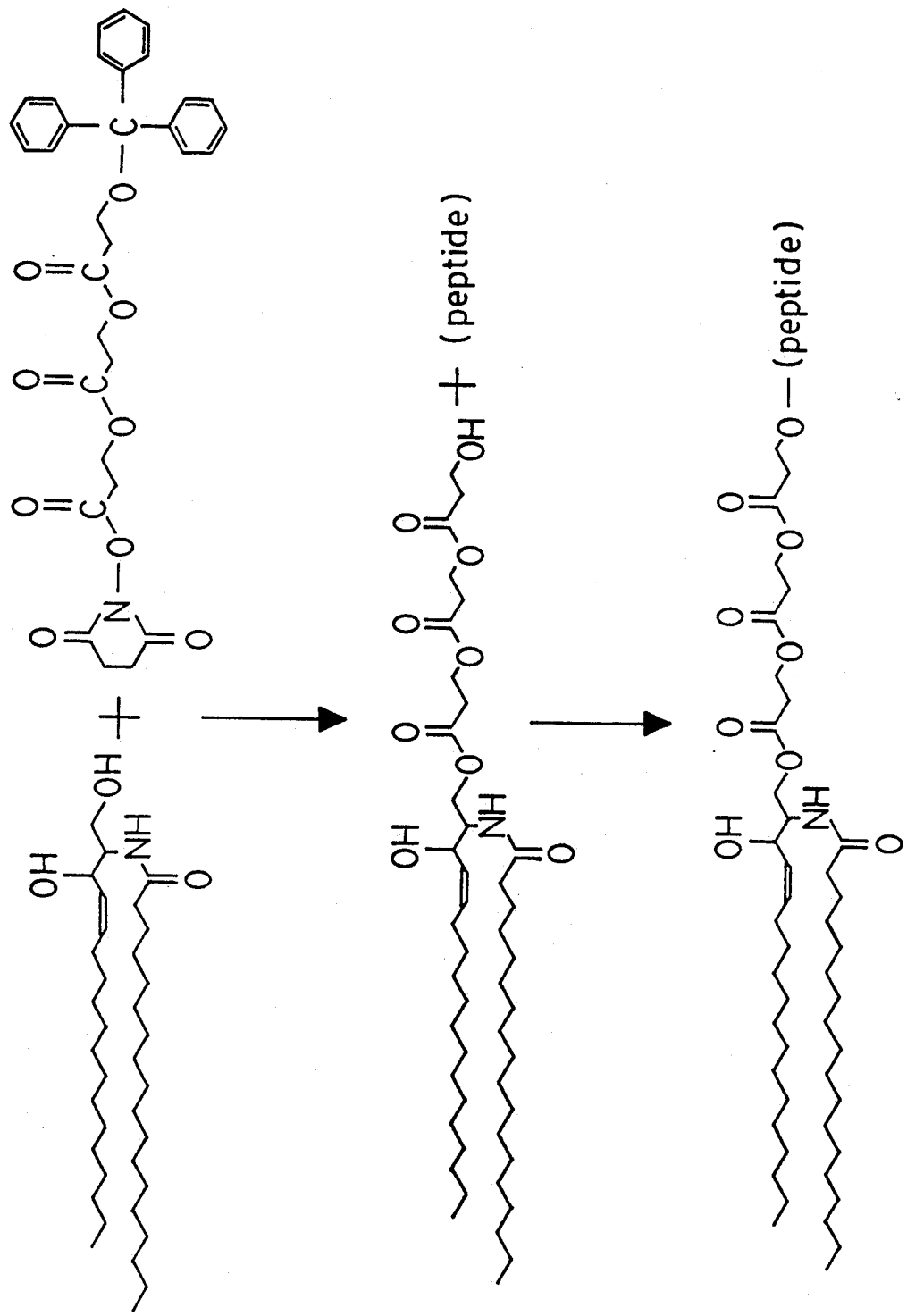
FIG. 3 depicts the synthetic scheme put forth in Example 3.
Figure 5:
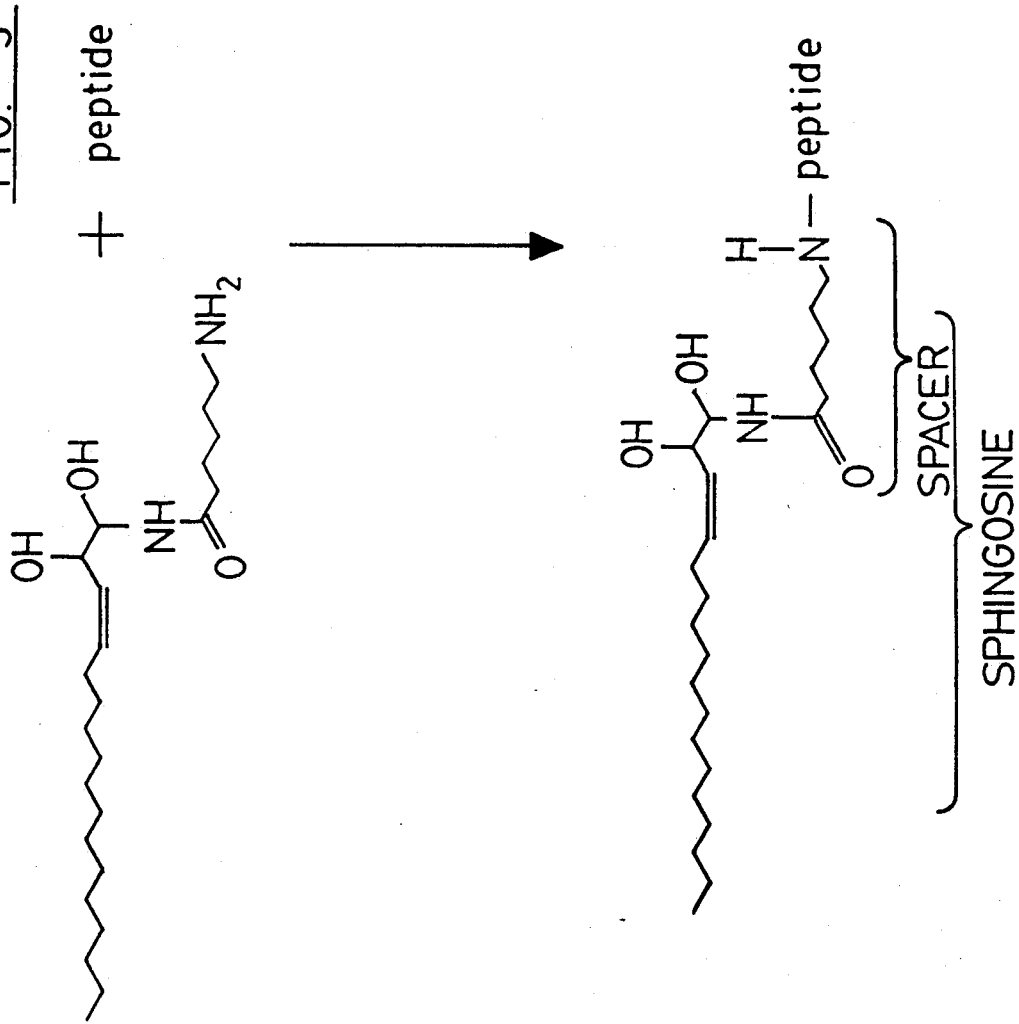
FIG. 5 depicts the synthetic scheme put forth in Example 5.
Figure 6:
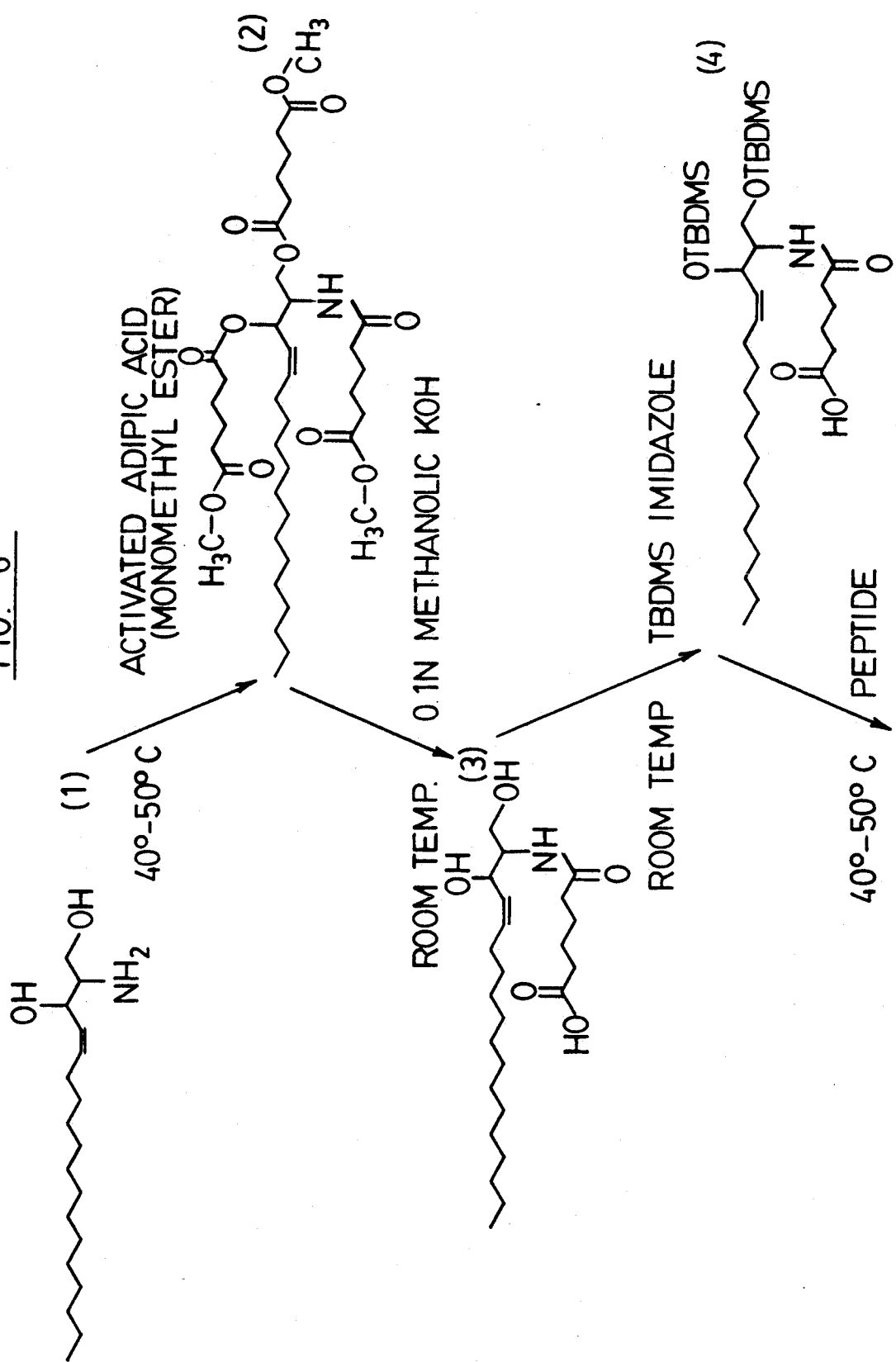
FIG. 6 depicts the synthetic scheme put forth in Example 6.

The present invention provides methods for facilitating the entry of antigenically-active peptides into cells and for delivering such peptides to the appropriate intracellular organelles for immunological processing and antigen presentation. This is achieved by conjugating the desired antigenically-active peptide to a polar lipid carrier and administering this conjugate to an animal by standard techniques.

The activity of these conjugates can be further refined by attaching the polar lipid carrier to an antigenically-active peptide through a spacer group having a first and a second end. Specifically, this is achieved through first linking the polar lipid to the first end of the spacer group through a linker functional group. In such a case, the antigenically-active peptide is then bound to a second end of the spacer group through a second linker functional group. This polar lipid/spacer/antigenically-active peptide conjugate will provide enhanced flexibility and versatility in targeting peptide delivery and in facilitating peptide release upon reaching the appropriate intracellular target site.

Experimentally, it was found that fluorescent ceramide is distributed differentially in different cells. These results suggest that by the proper choice of polar lipid conjugate, intracellular targeting of antigenically-active peptides can be achieved. This result enables the delivery of antigenically-active peptides to nascent major histocompatibility complex protein molecules of both types (class I and class II). Thus, antigen presentation of such antigenically-active peptides can be achieved, allowing activation of both humoral and cellular immunity.

The invention specifically provides methods for preparing and administering vaccines against pathological microorganisms, and compositions comprising such vaccines. Vaccines provided by the invention include but are not limited to vaccines against poliovirus, measles virus, rabies virus, the rubella virus, human immunodeficiency virus, Epstein-Barr virus, varicella zoster, herpes simplex virus, hepatitis virus, human papilloma virus, the microorganisms responsible for diphtheria, malaria, scarlet fever, viral and bacterial pneumonia, whooping cough, scrapie, and other diseases.

Alternatively, pathological conditions (such as autoimmune disease) may be alleviated by the selective blocking of self-antigen presentation by the administration of the appropriate blocking peptides covalently linked to an appropriate polar lipid carrier. Autoimmune diseases intended for this treatment include but are not limited to diabetes type I, lupus erythematosus, rheumatoid arthritis, encephalomyelitis, Hashimoto's disease, oophoritis, orchiditis, myasthenia gravis, polyneuritis, polymyositis, dermatomyositis, scleroderma, rheumatoid carditis, Sjögen's syndrome, and autoimmune hemolytic anemias.

Similarly, tissue and organ transplantation rejection can be inhibited by the selective blocking of nonself-antigen presentation by the administration of the appropriate blocking peptides covalently linked to an appropriate polar lipid carrier. The methods of this invention are intended to be useful in inhibiting rejection of transplanted organs and tissues including kidney, liver, pancreas, lung, heart, cornea, bone marrow, skin, endocrine organs, and portions of the gastrointestinal tract, although this is not intended to be an exhaustive listing of all the uses for this aspect of the invention.

Animals to be treated with polar lipid-antigenically active peptide conjugates using the methods of the invention are intended to include all vertebrate animals, preferrably domesticated animals, such as cattle, horses, goats, sheep, fowl, fish, household pets, and others, as well as wild animals, and most preferably humans.

An antigenically-active peptide, as used herein, is defined as including, but not necessarily limited to any peptide, comprising 4-100 amino acids (including naturally-occurring amino acids, amino acid analogues and derivatives thereof), that is capable of eliciting or inhibiting and immunological response in an animal, preferably a human being. More specifically, such antigenically-active peptides are characterized by their capacity to induce, augment or block (i.e., down-regulate) humoral and/or cellular immune responses in vivo. Such peptides include peptides whose amino acid sequence is known and can be chemically synthesized in vitro, or produced using recombinant genetic means, as well as mixtures of such peptides. Alternatively, antigenic proteins can be chemically or enzymatically degraded in vitro, and mixtures of peptides so produced then used for preparing peptide-polar lipid conjugates of the invention. Covalently-linked multimers of such antigenically-active peptides are also encompassed by the invention. Representation specific binding peptide sequences include but are not limited to:

| Vaccines | |
|---|---|
| PKYVKQNTLKLAT | (influenza virus hemagglutinin, residues 307–319) |
| IYATVAGSL | (influenza virus hemagglutinin, residues 523–531) |
| QYIKANSKFIGITE | (tetanus toxoid, residues 830–843) |
| SLSDLRGYVYQGLKSGNVS | (VSV nucleocapsid, reisdues 47–65) |
| TYQRTRALVRTG | (influenza virus nucleoprotein, residues 174–158) |
| IASNENMETMESSTLE | (influenza virus nucleoprotein, residues 365–380) |
| SRYWAIRTR | (influenza virus nucleoprotein, residues 383–391) |
| SYVPSAEQI | (P. yoelii CSP, residues 276–288) |
| SYIPSAEKI | (P. berghi CSP, residues 249–260) |
| NANP | (P. falciparum CSP) |
| ILKEPVHGV | (HIV reverse transcriptase, residues 461–469) |
| FLQSRPEPT | (HIV gag protein, residues 446–454) |
| AMQMLKE | (HIV gag protein, residues 193–199) |
| PIAPGQMRE | (HIV gag protein, residues 219–227) |
| QMKDCTERQ | (HIV gag protein, residues 418–426) |
| KRWIILGLNKIV | (HIV gag protein, residues 265–276) |
| GRAFVTIGK | (HIV gp120, residues 314–322) |
| CCTKPTEGNCTC | (hepatatis B surface antigen, residue 138–149) |
| KYALAEASLKMAEPNQFRGKELP | (HSV glycoprotein D-1, residues 1–23) |
| KYALAEPSLKMAEPNQFRGKNLP | (HSV glycoprotein D-2, residues 1–23) |
| RYNRNAVPNLRGELQVLAQKVARTLP | (FMDV VP1, residues (135–160) |
| SGVENPGGYCL | (lymphocyte choriomeningitis virus glycoprotein, residues 272–282) |

| Autoimmunity | |
|---|---|
| DMGHGLRLIHYSYDVNSTEKG | (T-cell receptor V$\beta$8) |
| APGGTLQQLFYSFNVGQSELV | (T-cell receptor V$\beta$8) |
| GRTQDENPVVHPPKNIVTPRTPPP | (myelin basic protein) |
| ASQKRPSQRHG | (myelin basic protein) |
| IRGERA | (human histone H3) |
| RRYQKSTEL | (human histone H3) |
| RRIKEIVKK | (human heat shock protein 89$\alpha$) |
| RRVKEVVKK | (human heat shock protein 89$\beta$) |
| NLLDGDPRDFVDNS | (EGF receptor, residues 516–529) |
| PEFLEQRRAAVDTYC | (Es $\beta$ chain) |

| Transplantation | |
|---|---|
| RYLENGKET | (HLA-24, residues 170–179) |
| RYLKNGKET | (HLA-Cw3, residues 170–179) |
| PPKTHVTHHP | (HLA-B27, residues 182–191) |
| GSHSMRYFHTSV | (HLA-B27, residues 1–12) |
| SYFPEITHI | (self peptide[1]) |
| KRFEGLTQR | (self peptide[2]) |
| RRFTRPEH | (self peptide[2]) |
| RRISGVDRY | (self peptide[2]) |
| ARLFGIRAK | (self peptide[2]) |

[1]Falk et al., 1991, Nature 351: 290–296)
[2]Jardetzky et al., 1991, Nature 353: 326–329)
[Single letter abbreviations for amino acids can be found in Zubay, 1988, Biochemistry 2d ed., (MacMillan Publishing: New York), p. 33.]

A polar lipid carrier, as defined herein will be taken to mean any polar lipid having an affinity for, or capable of crossing, a biological membrane, including but not limited to sphingosine, ceramide, phosphatidyl choline, phosphatidyl glycerol, phosphatidyl ethanolamine, phosphatidyl inositol, phosphatidyl serine, cardiolipin, phosphatidic acid, sphingomyelin and other sphingolipids.

A linder functional group is defined as any functional group for covalently binding the polar lipid carrier or the antigenically-active peptide to the spacer group. These groups can be designated either "weak" or "strong" based on the stability of the covalent bond which the linker functional group will form between the spacer and either the polar lipid carrier or the antigenically-active peptide. The weak functionalities include, but are not limited to phosphoramide, phosphoester, carbonate, amide, carboxyl-phosphoryl anhydride, ester and thioester. The strong functionalities include, but are not limited to ether, thioether, amine, amide and ester. The use of a strong linder functional group between the spacer group and the antigenically-active peptide will decrease the rate at which the peptide will be released at the target site, whereas the use of a weak linker functional group between the spacer group and the peptide may act to facilitate release of the peptide at the target site. Enzymatic release is another possiblity, however, the rate of release of the peptide would not necessarily be correlated with bond strength.

A spacer group may be broadly defined as any chemical group designed to facilitate the attachment of the peptide/polar lipid conjugates to a target cell and/or the release of the peptide at the desired target site. Such spacers may facilitate enzymatic release at certain intracellular sites. Some spacers may simply present an "unhindered inhibitor," still linked to the carrier-spacer conjugate, to a target enzyme. Spacer groups, as described herein, include, but are not limited to adipic acid, aminohexanoic acid, polyamides, polyethylenes, and short functionalized polymers having a carbon backbone which is one to about twelve carbon molecules in length. Throughout the description of the Examples, it will be assumed that all intermediate compounds will be isolated using standard methods.

EXAMPLE 1

An antigenically-active peptide is conjugated to sphingosine as follows. Sphingosine is reacted with 1,3 bis(trimethylsilyl)urea as described by Verbloom et al. (1981, Synthesis 1032: 807–809) to give a trimethylsilyl derivative of sphingosine. The sphingosine derivative is then conjugated with the antigenically-active peptide in which the terminal amine and any of the constituent amino acid sidechain reactive amines are covered by tBoc protecting groups in the presence of diethylazodicarboxylate (DEAD) and triphenyl phosphine as described by Kishimoto (1975, Chem. Phys. Lipids 15: 33–36). The sphingosine/peptide conjugate is then reacted in the presence of pyridine hydrofluoride as described by Matsuura et al. (1976, J. Chem. Soc. Chem. Comm. pg. 451–459) to remove the tBoc protecting group, to yield the antigenically-active peptide covalently linked to sphingosine through an amide bond.

EXAMPLE 2

An antigenically-active compound consisting of ceramide conjugated to a first end of an antigenically-active peptide through an ester linker functional group or an amide linker functional group. The antigenically-active peptide has both a carboxyl terminus and an amino terminus, the amino terminus being protected by a tBoc group. The antigenically-active peptide is conjugated through its carboxyl terminus to ceramide forming an ester linkage, as described by Anderson et al. (1963, J. Chem. Soc. Chem. Comm. 85: 3039). The amino terminus of the antigenically-active peptide is then deprotected according to the method of Matsuura et al. (1976, J. Chem. Soc. Comm. pg. 451).

EXAMPLE 3

An antigenically-active peptide compound wherein ceramide is conjugated to a first end of an oligomeric 3-hydroxy-propanoic acid spacer through an ester functional group, and wherein the antigenically-active peptide is conjugated to a second end of the polyester spacer through an amide linkage to the amino terminus of the antigenically-active peptide. The polyester spacer is first obtained, having a carboxyl group at a first end and a triphenylmethyl group esterified to a second end. This spacer is conjugated to ceramide at its first end through an ester functional linker group according to the method of Anderson et al. (1963, J. Am. Chem. Soc. 85: 3039). This compound is then conjugated through the second end of the spacer compound to the antigenically-active peptide by means of a amide linkage according to the method of Verbloom et al. (1981, Synthesis 1032: 807–809).

EXAMPLE 4

An antigenically-active peptide compound wherein phosphatidic acid, phosphatidyl choline, phosphatidyl serine, phosphatidyl inositol, phosphatidyl glycerol or phosphatidylethanolamine is linked through a phosphoester linker functional group to the antigenically-active peptide. Phosphatidic acid, phosphatidyl choline, phosphatidyl serine, phosphatidyl inositol, phosphatidyl glycerol or phosphatidyl ethanolamine is conjugated to the carboxyl terminus of the antigenically-active peptide according to the method of Salord et al. (1986, Biochim. Biophys. Acta 886: 64–75).

EXAMPLE 5

An antigenically-active peptide compound wherein aminohexanoyl sphingosine is conjugated to the carboxyl terminus of peptide the antigenically-active peptide. Aminohexanoyl sphingosine is conjugated with the antigenically-active peptide according to the method of Kishimoto (1975, Chem. Phys. Lipid 15: 33–36).

EXAMPLE 6

An antigenically-active peptide wherein sphingosine is conjugated to the amino terminus of the antigenically-active peptide through an adipic acid spacer. The primary amino and hydroxyl groups of sphingosine are acylated by reaction with adipic acid monomethyl ester overnight at 40°–50° C., followed by base hydrolysis of the ester (in 0.1N methanolic KOH). The free hydroxyl group of this intermediate is protected using t-butyl-dimethylsilane (TBDMS) by reaction overnight at room temperature. The antigenically-active peptide is then covalently linked to the free carboxyl end of the adipic acid spacer activated by reaction overnight at 40°–50° C. in the presence of carbonyl diimidazole (the details of this reaction may be found in Enzyme, vol.18, p. 310, 1974). The TBDMS protecting groups are then removed using tetrabutylammoniumfluoride to yield the antigenically-active peptide product.

EXAMPLE 7

An antigenically-active peptide compound wherein phosphatidic acid, phosphatidyl choline, phosphatidyl glycerol or phosphatidyl ethanolamine is linked through the sn-2 or sn-1 hydroxyl of the lysophospholipid to the antigenically-active peptide using the methods of Martin and Josey (1988, Tetrahedron Lett. 29:3631–3634). Briefly, the antigenically active peptide (whether or not covalently linked to a spacer moiety), or alternatively a fatty acid, is conjugated to the sn-1 hydroxyl of 3-sn-benzyl glycerol by reaction at 0° C. in the presence of dimethylaminopyridine/dicyclohexyl-carbodiimide/methylene chloride (DMAP/DCC/CH$_2$Cl$_2$). A fatty acid, or alternatively the antigenically-active peptide (whether or not covalently linked to a spacer moiety), is then conjugated to the sn-2 hydroxyl of 3-sn-benzyl-1-sn-substituted glycerol at 20° C. in the presence of DMAP/DCC/CH$_2$Cl$_2$. The 3-sn position is then deprotected at 45° C. in ethanol/acetic acid in the presence of platinum black and H$_2$. The appropriate polar head group is then phospho-esterified to the sn-3 position in the presence of phenyldichlorophosphite/diisopropylethylamine/tetrahydrofuran at −78° C.

Alternatively, the antigenically-active peptide (whether or not covalently linked to a spacer moiety), can be conjugated to phospholipid following enzymatic deacylation of a diacylphospholipid with phospholipase A$_2$ using the method of Eibi et al. (1983, Meth. Enzymol. 98: 623).

EXAMPLE 8

Antigenically-active peptide-polar lipid conjugates of the invention are used as follows. For use as a vaccine, the conjugate, the naked peptide and a negative control (saline) are administered to an animal using both optimal and suboptimal dosages and the most appropriate route of administration. After an optimal time period (determined from the nature of the immunological response to be elicited), both sera and lymphoid cells are collected from the animal and tested for reactivity to the antigen. Lymphoid cells are isolated using conventional methods (Ficoll-Hypaque density gradient centrifugation) and tested for cytotoxic activity against control autologous macrophage/monocyte preparations exposed to and subsequently presenting the original peptide antigen. Testing is performed using the $^{51}$Cr release assay of Malkovsky et al. (1982, Nature 300: 652-655). Antibody response is tested using standard radioimmunoassay methods (see, Brenner et al., 1984, Eur. J. Immunol. 14: 1021-1027). Briefly, Linbro flexible plates are coated with the specific peptide antigen by overnight incubation of a peptide solution (1 mg/mL) in phosphate buffered saline (PBS). Nonspecific binding is then blocked by treatment of the plates with a solution of 0.2% bovine serum albumin and 0.2% gelatin in PBS. The plates are then washed, sera to be tested is then added, and the plates re-washed after incubation of the sera on the plates. $^{125}$I-labeled anti-IgG and anti-IgM antibodies are then added, the plates washed and bound radioactivity counted. The amount of peptide-antigen specific antibody present on each plate is then calculated relative to a standard curve prepared with known amounts of anti-peptide antibody. From these experiments the titre of specific antibody against each peptide antigen is calculated for each experimental sera tested.

For use in preventing transplant rejection or to treat autoimmune disease, the appropriate administration protocol is determined by vaccination of an animal as described above. After an empirically-determined optimal time period (determined from the nature of the immunological response to be elicited), both sera and lymphoid cells are collected from the animal and tested for reactivity to either self-antigen (for autoimmune disease uses) or heterologous transplantation antigens, as described above.

It should be understood that the foregoing disclosure emphasizes certain specific embodiments of the invention and that all modifications or alternatives equivalent thereto are within the spirit and scope of the invention as set forth in the appended claims.

What is claimed is:

1. A composition of matter comprising a peptide, a polar lipid carrier, two linker functional groups and a spacer, wherein the spacer has a first end and a second end and wherein the polar lipid is attached to the first end of the spacer through a first linker functional group and the peptide is attached to the second end of the spacer through a second linker functional group.

2. The compostion of matter of claim 1 wherein the peptide is an antigenically active peptide.

3. A composition of matter according to claim 1 wherein the spacer allows the peptide to act without being released at an intracellular site and wherein the first linker functional group attached to the first end of the spacer is strong and the second linker functional group attached to the second end of the spacer is weak.

4. A composition of matter according to claim 1 wherein the spacer allows the peptide to facilitate hydrolytic release of the peptide at an intracellular site and wherein the first linker functional group attached to the first end of the spacer is strong and the second linker functional group attached to the second end of the spacer is weak.

5. A composition of matter according to claim 1 wherein the spacer allows the spacer to facilitate enzymatic release of the peptide at an intracellular site and wherein the first linker functional group attached to the first end of the spacer is strong and the second linker functional group attached to the second end of the spacer is weak.

6. A composition of matter according to claim 1 wherein the polar lipid is sphingosine, ceramide, phosphatidyl choline, phosphatidyl glycerol, phosphatidyl ethanolamine, phosphatidyl inositol, phosphatidyl serine, cardiolipin and phosphatidic acid.

7. A composition of matter comprising a peptide having a first functional linker group, and a polar lipid carrier having a second functional linker group, wherein the peptide is covalently linked to the polar lipid carrier by a chemical bond between the first and second functional linker groups.

8. A composition of matter according to claim 7 wherein the first functional linker group is a hydroxyl group, a primary or secondary amino group, a phosphate group or substituted derivatives thereof or a carboxylic acid group.

9. A composition of matter according to claim 7 wherein the second functional linker group is a hydroxyl group, a primary or secondary amino group, a phosphate group or substituted derivatives thereof or a carboxylic acid group.

10. A composition of matter according to claim 7 wherein the polar lipid is sphingosine, ceramide, phosphatidyl choline, phosphatidyl glycerol, phosphatidyl ethanolamine, phosphatidyl inositol, phosphatidyl serine, cardiolipin and phosphatidic acid.

11. The composition of matter of claim 7 wherein the peptide is an antigenically active peptide.

12. A method of immunizing an animal against a pathogenic microorganism, comprising the step of inoculating the animal with the composition of matter of claim 2 in a pharmaceutically acceptable carrier and in an amount sufficient to elicit an immunological response in the animal.

13. The method of claim 12 wherein the animal is a human.

14. A method of immunizing an animal against a pathogenic microorganism, comprising the step of inoculating the animal with the composition of matter of claim 11 in a pharmaceutically acceptable carrier and in an amount sufficient to elicit an immunological response in the animal.

15. The method of claim 14 wherein the animal is a human.

16. A method of alleviating an autoimmune disease in an animal, comprising the step of inoculating the animal with the composition of matter of claim 2 in a pharmaceutically acceptable carrier and in an amount sufficient to inhibit the autoimmune response in the animal.

17. The method of claim 16 wherein the animal is a human.

18. A method of alleviating an autoimmune disease in an animal, comprising the step of inoculating the animal with the composition of matter of claim 11 in a pharmaceutically acceptable carrier and in an amount sufficient to inhibit the autoimmune response in the animal.

19. The method of claim 18 wherein the animal is a human.

20. A method of preventing tissue or organ transplant rejection in an animal, comprising the step of inoculating the animal with the composition of matter of claim 2 in a pharmaceutically acceptable carrier and in an amount sufficient to inhibit transplant rejection in the animal.

21. The method of claim 20 wherein the animal is a human.

22. A method of preventing tissue or organ transplant rejection in an animal, comprising the step of inoculating the animal with the composition of matter of claim 11 in a pharmaceutically acceptable carrier and in an amount sufficient to inhibit transplant rejection in the animal.

23. The method of claim 22 wherein the animal is a human.

* * * * *